US00PP34323P2

(12) United States Plant Patent
Moon

(10) Patent No.: US PP34,323 P2
(45) Date of Patent: Jun. 14, 2022

(54) ***QUERCUS* TREE NAMED 'QNMTF2'**

(50) Latin Name: *Quercus nuttallii*
Varietal Denomination: QNMTF2

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 17/235,641

(22) Filed: Apr. 20, 2021

(51) Int. Cl.
*A01H 5/00* (2018.01)
*A01H 6/00* (2018.01)

(52) U.S. Cl.
USPC ..... Plt./225

(58) Field of Classification Search
USPC ..... Plt./216, 225
See application file for complete search history.

*Primary Examiner* — Karen M Redden
(74) *Attorney, Agent, or Firm* — Cassandra Bright

(57) ABSTRACT

A new and distinct *Quercus nuttallii* tree named 'QNMTF2' is disclosed, characterized by a unique, upright, columnal form with a dense canopy. Fall foliage is yellow, with leaves dropping cleanly in the Fall. A fast growth rate has been observed. The new variety is a *Quercus* tree, typically used for landscapes and gardens.

3 Drawing Sheets

Figure 1:
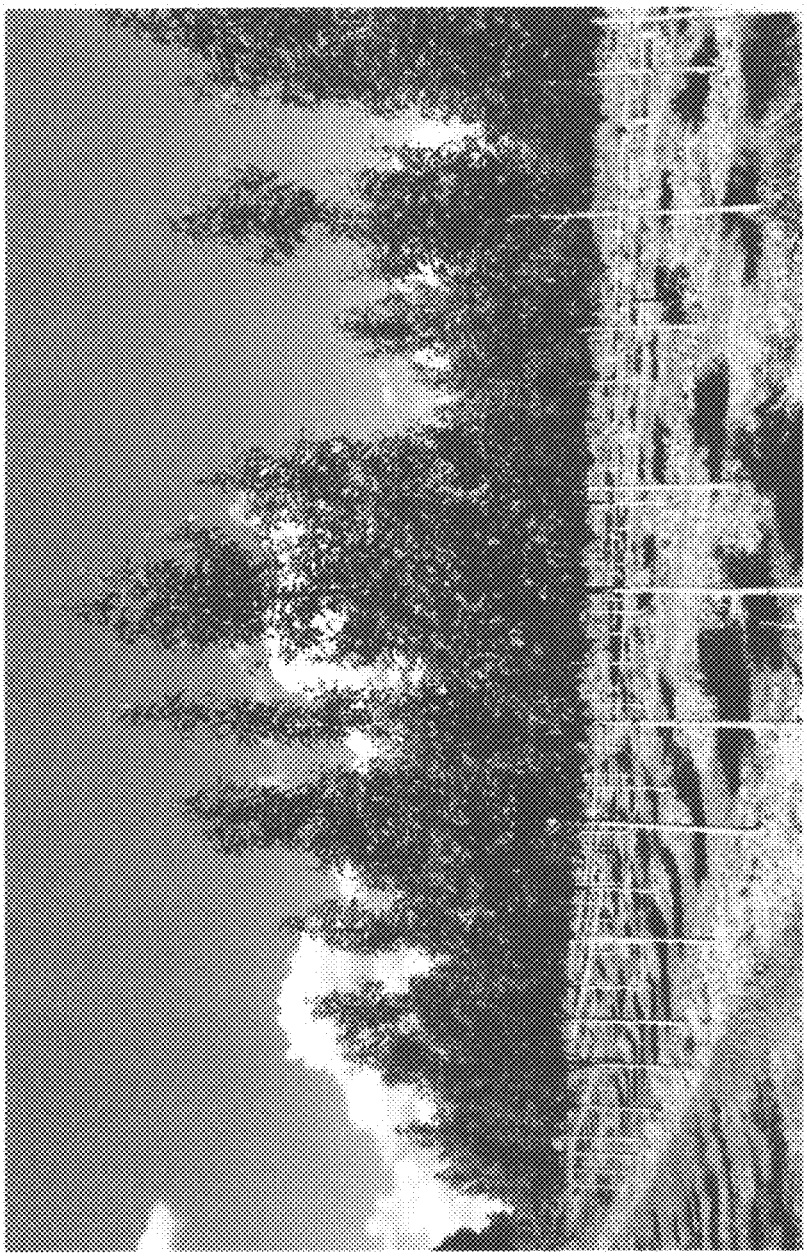

Latin name of the genus and species: *Quercus nuttallii*.
Variety denomination: 'QNMTF2'.

BACKGROUND OF THE INVENTION

The new cultivar is a product of a planned breeding program. The new variety was discovered growing as a seedling among a group of crossbred *Quercus nuttallii* trees at a tree farm in Washington, Ga. The inventor made this discovery in the Summer of 2014. The exact seed and pollen parents cannot be identified.

Asexual reproduction by grafting of the new cultivar 'QNMTF2' was first performed during February of 2015 at a farm in Washington, Ga. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that the new variety represents a new and improved variety of *Quercus nuttallii* tree as particularly evidenced by the fastigiate growth habit. These genetic traits can be consistently reproduced by asexual propagation.

SUMMARY OF THE INVENTION

The cultivar 'QNMTF2' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'QNMTF2' grown in Washington, Ga. These characteristics in combination distinguish 'QNMTF2' as a new and distinct *Quercus nuttallii* cultivar:

1. Upright columnal form.
2. Faster growth rate.

3. Yellow fall foliage color.
4. Clean leaf drop in Fall.
5. Dense full canopy.
6. Fastigiate in structure.
7. Larger leaf.

PARENT COMPARISON

The exact parent varieties cannot be identified.

COMMERCIAL COMPARISON

Plants of the new cultivar 'QNMTF2' are similar to plants of *Quercus nuttallii* 'QNSTG', U.S. Plant Pat. No. 19,858, in most horticultural characteristics, however, plants of the new cultivar 'QNMTF2' differ in the following:

1. The new variety has a columnar, fastigiate growth habit, while this comparator has an upright growth habit.
2. The new variety has green new foliage; this comparator produces red new foliage.
3. Fall foliage color of the new variety is yellow; Fall foliage color of this comparator is Orange-Red and Yellow-Orange.

Plants of the new cultivar 'QNMTF2' are similar to plants of *Quercus nuttallii* 'QNSTC', U.S. Plant Pat. No. 16,401, in most horticultural characteristics, however, plants of the new cultivar 'QNMTF2' differ in the following:

1. The new variety has a columnar, fastigiate growth habit, while this comparator has a slightly upright to outwardly branching growth habit.
2. Fall foliage color of the new variety is yellow; Fall foliage color of this comparator is red.

Plants of the new cultivar 'QNMTF2' are similar to plants of *Quercus nuttallii* 'QNSTD', U.S. Plant Pat. No. 16,254, in most horticultural characteristics, however, plants of the new cultivar 'QNMTF2' differ in the following:

1. The new variety has a columnar, fastigiate growth habit, while this comparator has a rounded growth habit.
2. The new variety has green new foliage; this comparator produces red new foliage.

3. Fall foliage color of the new variety is yellow; Fall foliage color of this comparator is Orange-Red and Yellow-Orange.

BRIEF DESCRIPTION OF THE PHOTOGRAPHS

The accompanying photograph in FIG. 1 illustrates the fastigiate growth of trees of the new variety.

Figure 2:
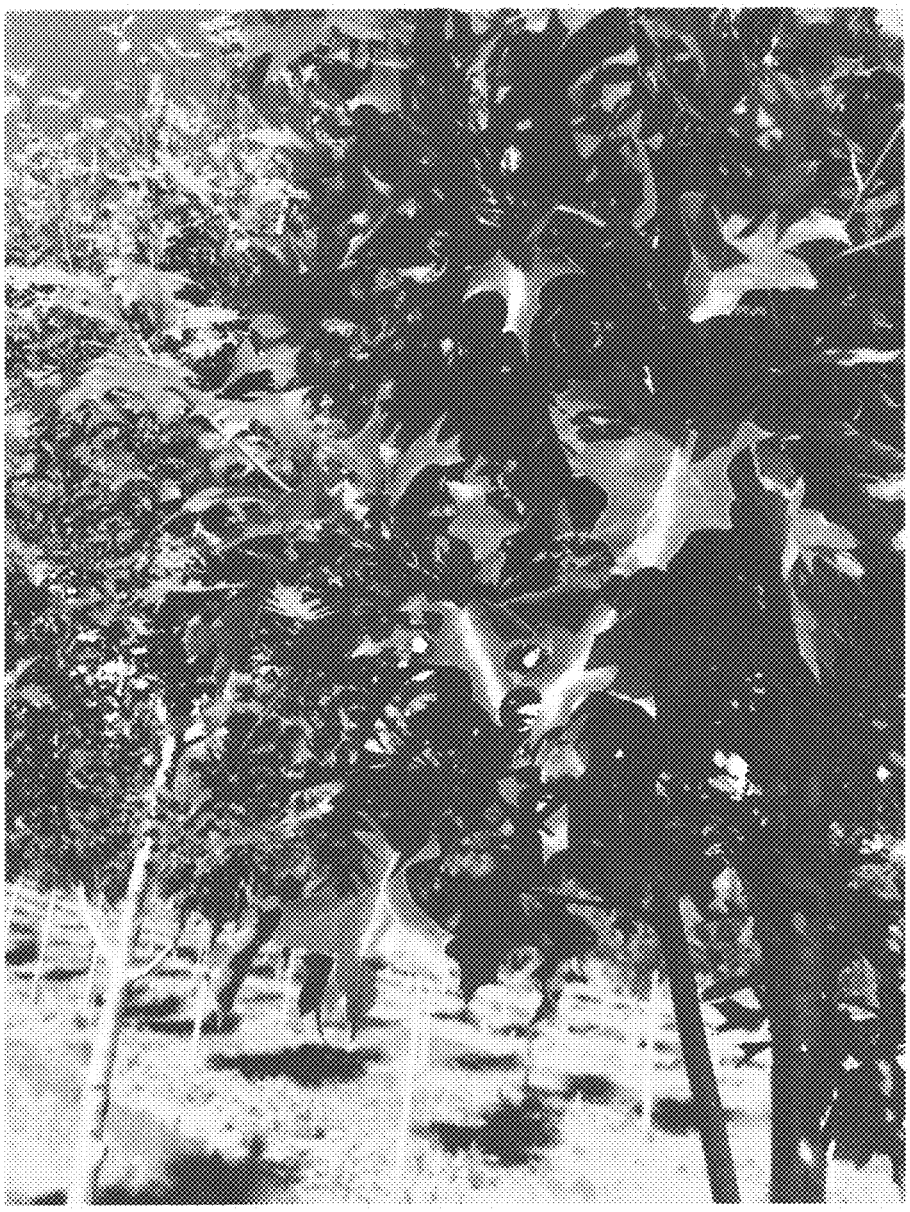

FIG. 2 illustrates a close-up view of the foliage during early Summer.

Figure 3:
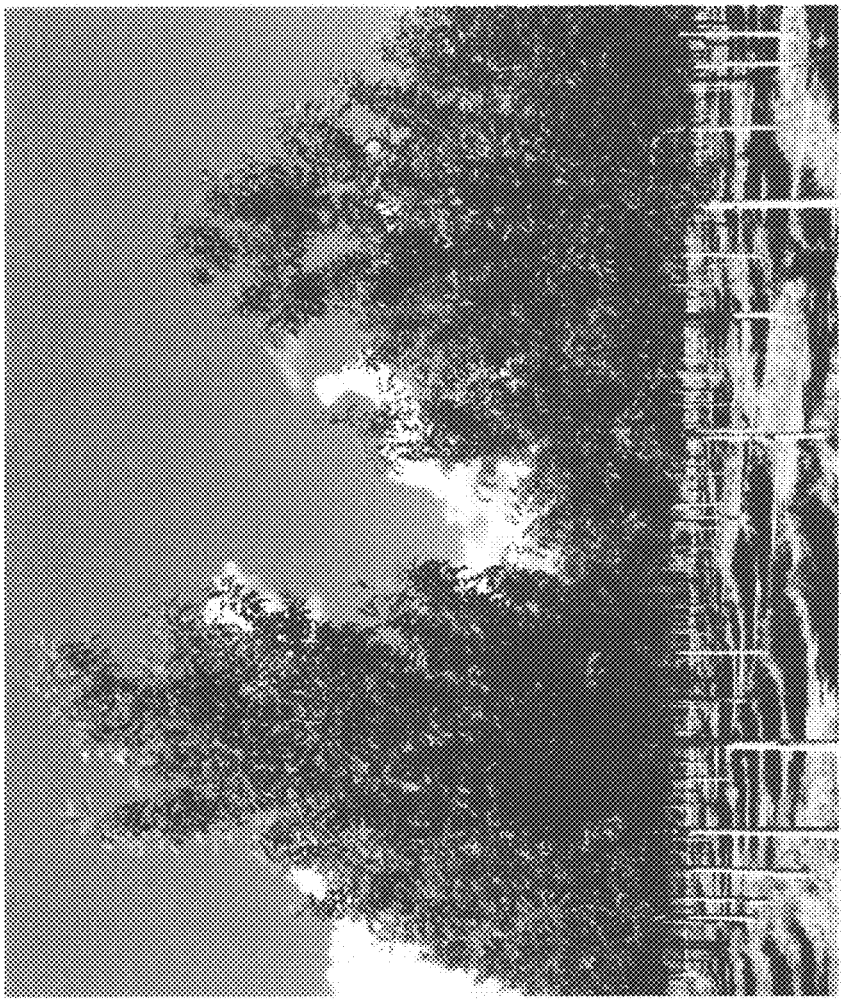

FIG. 3 illustrates two rows of trees; the new variety is on the left, an unnamed comparator is on the right. The much more upright growth habit of 'QNMTF2' can be seen in the row of trees on the left of the figure. All trees illustrated are field grown in Loganville, Ga.

Trees in FIGS. 1, 2 and 3 are approximately 3 to 5 years from planting into the field.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'QNMTF2' plants grown outdoors and in a nursery in Washington, Ga. Plants are approximately 2 years old, in a 3 gallon nursery container. Temperatures ranged from 5° C. to 10° C. at night to 18° C. to 27° C. during the day. Measurements and numerical values represent averages of typical plant types.

Botanical classification: *Quercus nuttallii* 'QNMTF2'.

PROPAGATION

Cleft grafting.

Root description: Woody. Brown roots not accurately measured with an R.H.S. Colour Chart.

TREE

Growth habit: Deciduous fastigiate tree.

Height: Approximately 12 feet at 3 years.

Spread: Approximately 5 feet at 3 years.

Aspect and angle: Branches at acute angles, 45 degrees or less.

Growth rate: Rapid.

Trunk characteristics:

*Diameter*.—About 2.5 inches measured at approximately 3 inches above soil level at 3 years.

*Color*.—Near RHS Greyed-Green 198A with large blotches 197A and 197B.

*Surface texture*.—Rippled.

FOLIAGE

Leaf:

*Arrangement*.—Alternate.

*Shape*.—Overall ovate, deeply lobed, 7 to 9 loves.

*Average length*.—Approximately 8 to 15 cm excluding petiole.

*Average width*.—Approximately 5 cm.

*Apex*.—Acute.

*Base*.—Obtuse or asymmetrical cordate.

*Margin*.—Deeply lobed with sharp tips at the apex of each lobe. Sinuses about 1.5 to 2.2 cm deep.

*Texture of top surface*.—Glabrous.

*Texture of lower surface*.—Glabrous.

*Color*.—Young foliage: Upper side: Near RHS Yellow-Green N144B. Under side: Near RHS Yellow-Green 145A. Mature foliage: Upper side: Near RHS Green 143A. Under side: Near RHS Green 143C.

*Venation*.—Type: Pinnate. Color: Venation color upper side: Near RHS Yellow-Green 144C. Venation color under side: Near RHS Yellow-Green N144A.

*Petiole*.—Length: Average 1.8 mm. Diameter: Average 2 mm. Texture: Glabrous. Color: Upper side: Near RHS Yellow-Green 144A. Under side: Near RHS Yellow-Green 144C.

FLOWER

Not observed.

REPRODUCTIVE ORGANS

Not observed.

OTHER CHARACTERISTICS

Disease/pest resistance: Neither resistance nor susceptibility to normal diseases and pests of *Quercus* has been observed.

Drought tolerance: No tolerance for drought observed. *Quercus nuttallii* can be moderately drought tolerance once established.

Temperature tolerance: USDA Zones 6 through 9.

Fruits/nuts: Not observed.

What is claimed is:

1. A new and distinct cultivar of *Quercus nuttallii* tree named 'QNMTF2' as herein illustrated and described.

* * * * *